United States Patent [19]

Kiwala et al.

[11] 4,343,791
[45] Aug. 10, 1982

[54] CYCLOHEXYL PHENETHYLETHER DERIVATIVES FOR COMBATTING TOBACCO BEETLES

[75] Inventors: Jacob Kiwala, Brooklyn, N.Y.; Richard J. Tokarzewski, Keyport, N.J.; Frederick L. Schmitt, Holmdel, N.J.; Mark A. Sprecker, Sea Bright, N.J.

[73] Assignee: International Flavors & Fragrances Inc., New York, N.Y.

[21] Appl. No.: 305,539

[22] Filed: Sep. 25, 1981

Related U.S. Application Data

[60] Division of Ser. No. 235,844, Feb. 19, 1981, Pat. No. 4,324,923, which is a continuation-in-part of Ser. No. 192,238, Sep. 30, 1980, Pat. No. 4,306,096.

[51] Int. Cl.$^3$ .................. A01N 25/00; A01N 31/00
[52] U.S. Cl. ............................. 424/84; 424/339
[58] Field of Search ........................... 424/84, 339

[56] References Cited

U.S. PATENT DOCUMENTS

2,411,428 11/1946 Hechenbleikner .................. 424/339
4,306,096 12/1981 Kiwala et al. ...................... 424/84

OTHER PUBLICATIONS

J. Econ. Ent. 66 (1973) pp. 369–370 & 1103–1105.
J. Econ. Ent. 63 (1970) p. 276.
Tobacco Int., vol. 182 (5) pp. 166–169, Mar. 1980.

Primary Examiner—Donald B. Moyer
Attorney, Agent, or Firm—Arthur L. Liberman

[57] ABSTRACT

Described is the genus of compounds defined according to the structure:

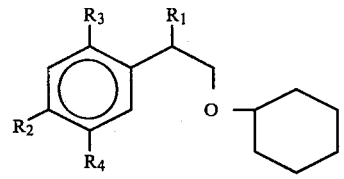

wherein $R_1$, $R_2$, $R_3$ and $R_4$ are the same or different and each represents methyl or hydrogen with the proviso that one of $R_2$, $R_3$ and $R_4$ is methyl and the other two of $R_2$, $R_3$ and $R_4$ are hydrogen which have been found to be useful in augmenting or enhancing the aroma of perfumes and perfumed articles as well as colognes and, in addition, in combatting tobacco beetles of the species *Lasioderma serricorne* (F.). Also described are novel processes for preparing such cyclohexyl phenethylether derivatives by reacting cyclohexene having the structure:

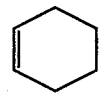

with a phenethyl alcohol derivative having the structure:

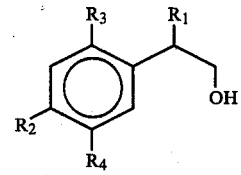

in the presence of an acid catalyst.

3 Claims, 19 Drawing Figures

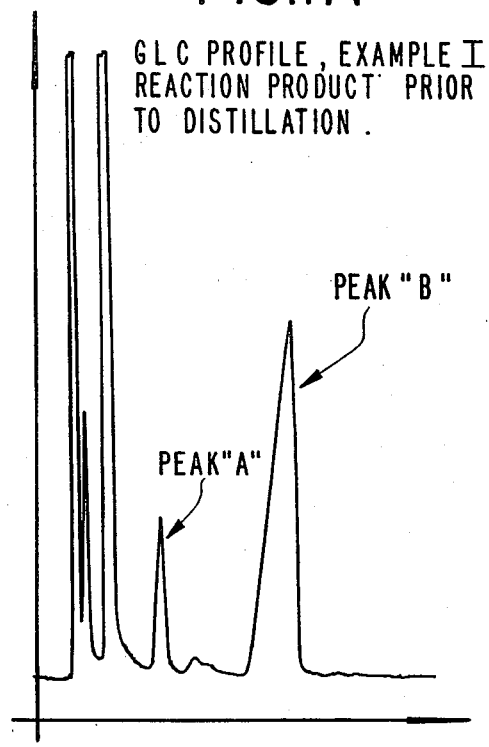
FIG.IA
GLC PROFILE, EXAMPLE I REACTION PRODUCT PRIOR TO DISTILLATION.
PEAK "A"
PEAK "B"
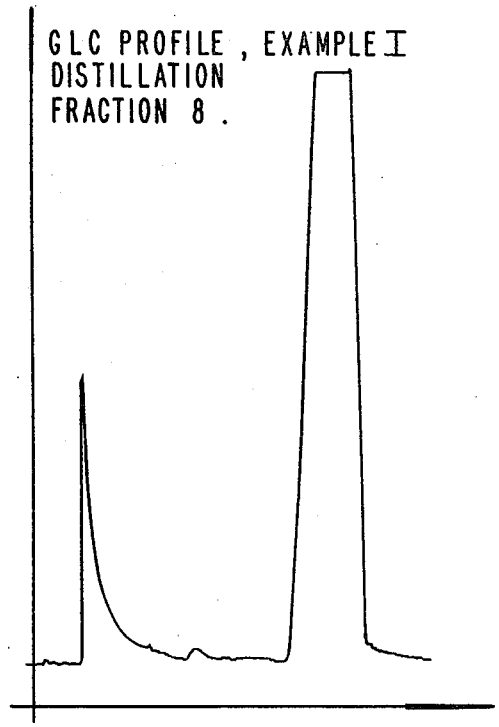
FIG.IB
GLC PROFILE, EXAMPLE I DISTILLATION FRACTION 8.
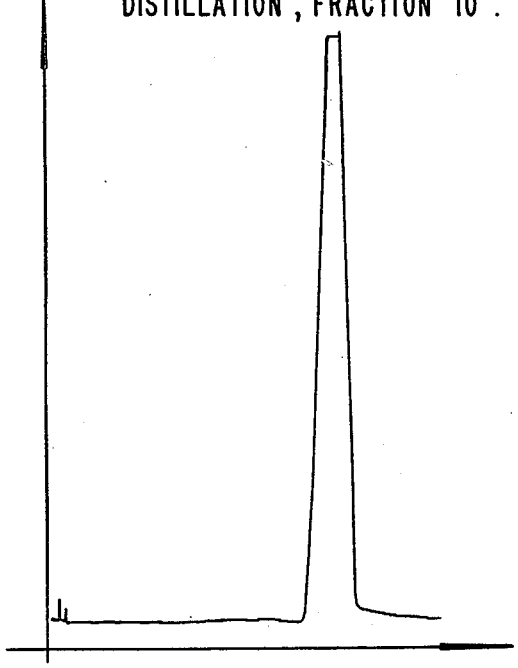
FIG.IC
GLC PROFILE FOR EXAMPLE I DISTILLATION, FRACTION 10.
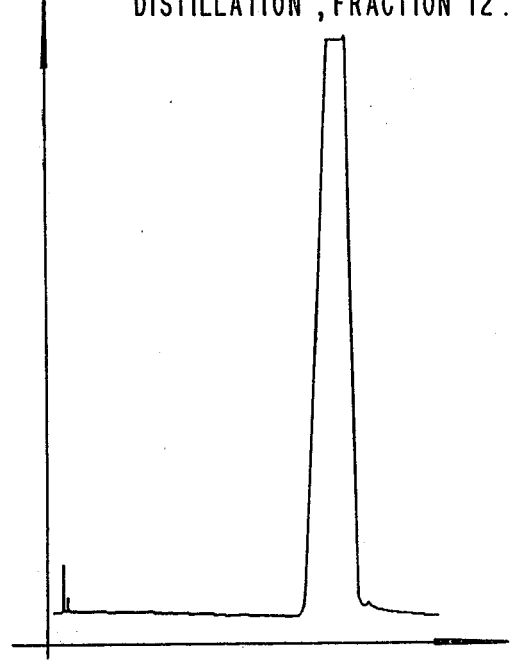
FIG.ID
GLC PROFILE FOR EXAMPLE I DISTILLATION, FRACTION 12.

FIG.2
NMR SPECTRUM FOR PEAK "A" OF EXAMPLE I.
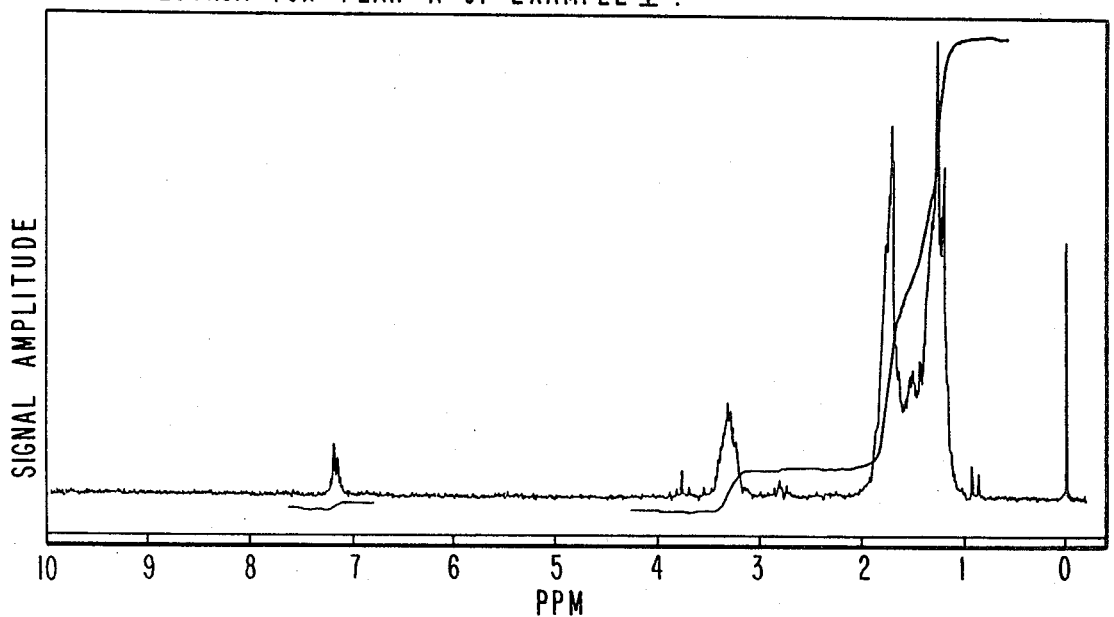
NMR SPECTRUM FOR PEAK "B" OF EXAMPLE I
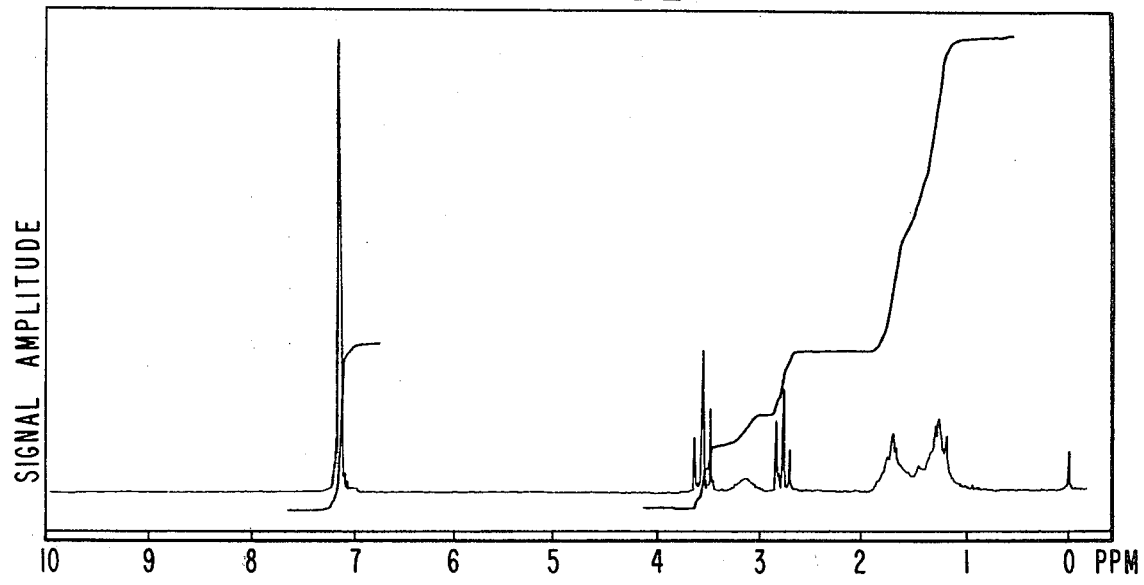
FIG.3

FIG.4
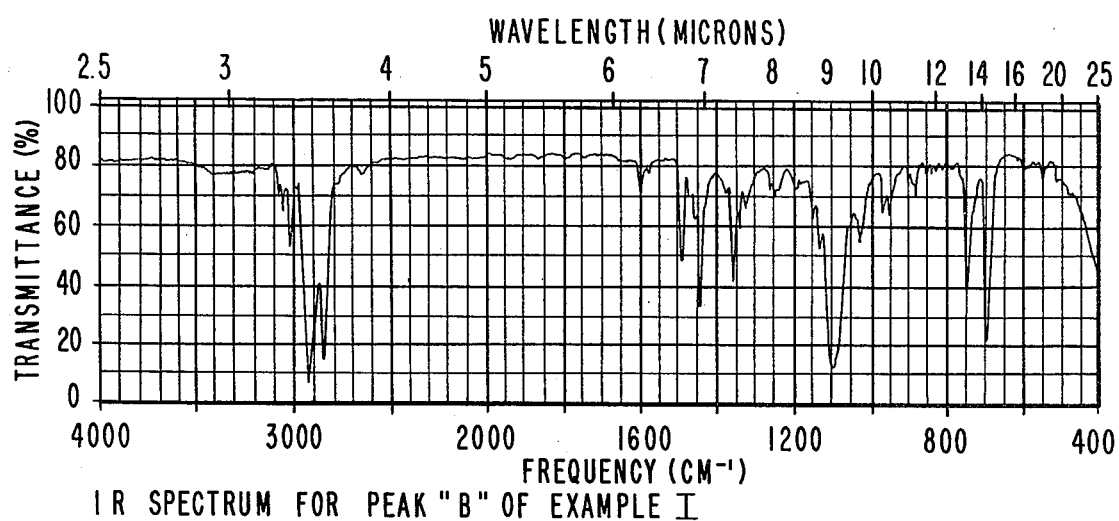
IR SPECTRUM FOR PEAK "B" OF EXAMPLE I
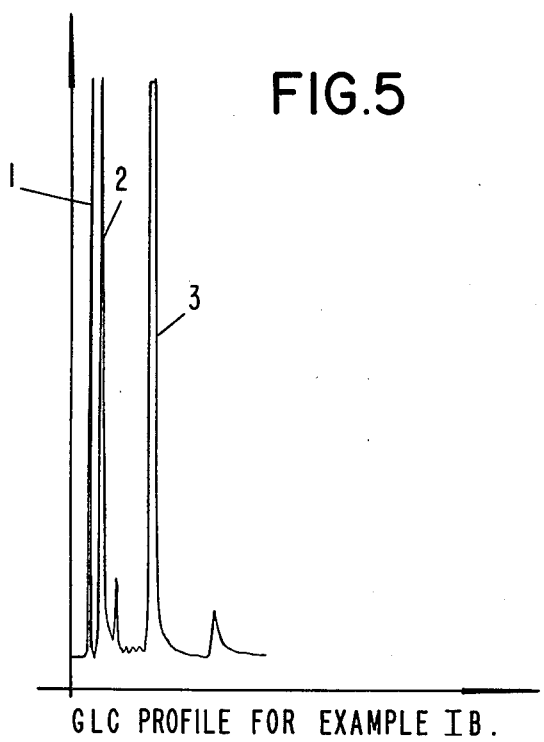
GLC PROFILE FOR EXAMPLE IB.
GLC PROFILE FOR FRACTION 7 OF EXAMPLE IB.

GLC PROFILE FOR FRACTION 10 OF EXAMPLE IB.

GLC PROFILE FOR FRACTION 22 OF EXAMPLE IB.

GLC PROFILE FOR EXAMPLE XVI. CRUDE PRODUCT

GLC PROFILE FOR FRACTION 8 OF EXAMPLE XVI.

FIG.8
NMR SPECTRUM FOR FRACTION 6 OF EXAMPLE XVI.
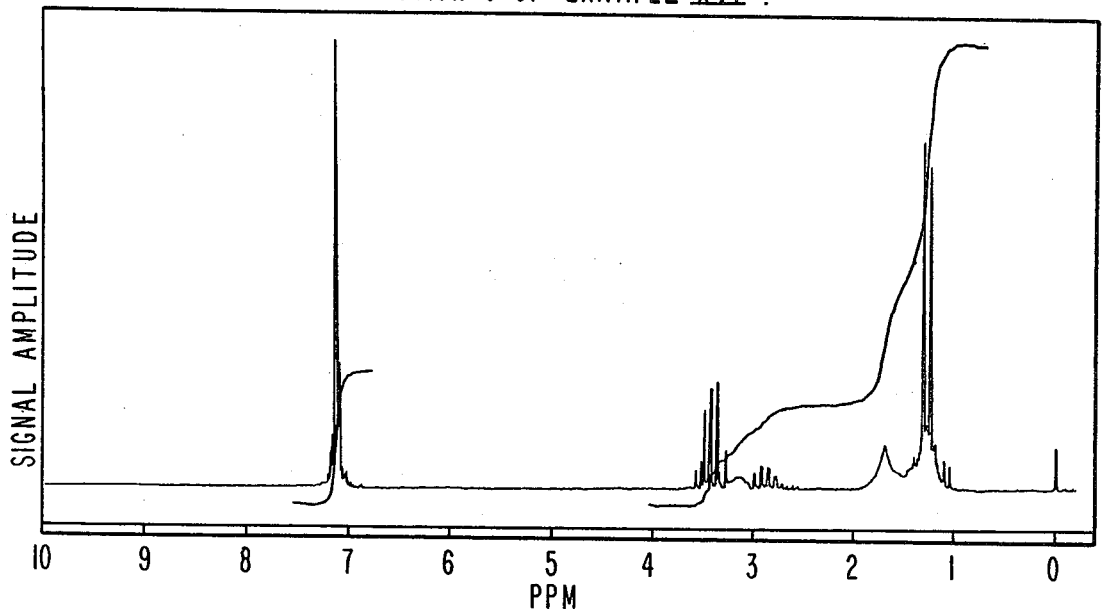
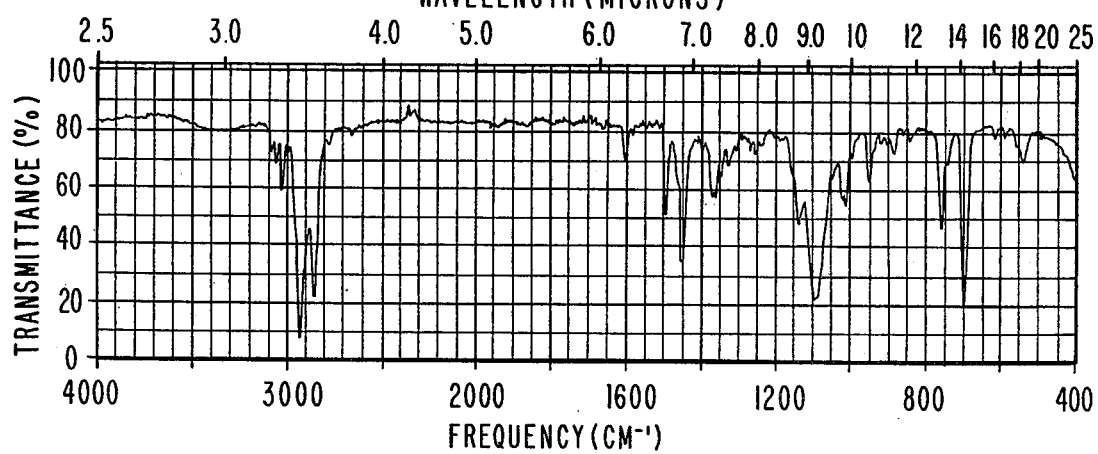
IR SPECTRUM FOR FRACTION 6 OF EXAMPLE XVI.
FIG.9

FIG.10 A
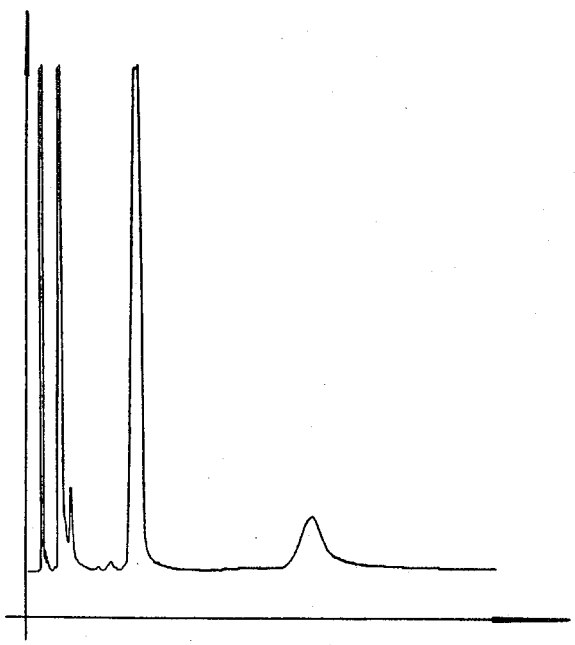
GLC PROFILE FOR EXAMPLE XVII CRUDE PRODUCT
FIG.10 B
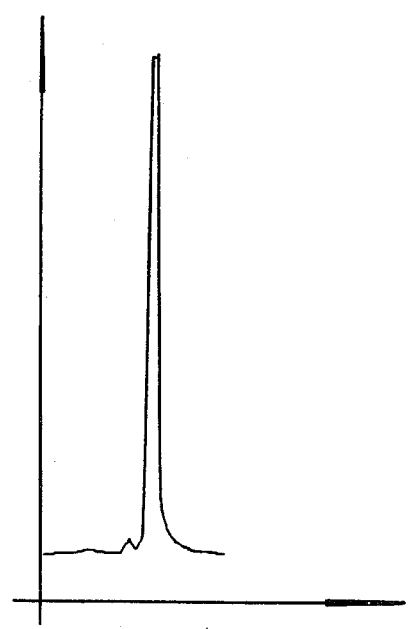
GLC PROFILE FOR FRACTION 8 OF EXAMPLE XVII.
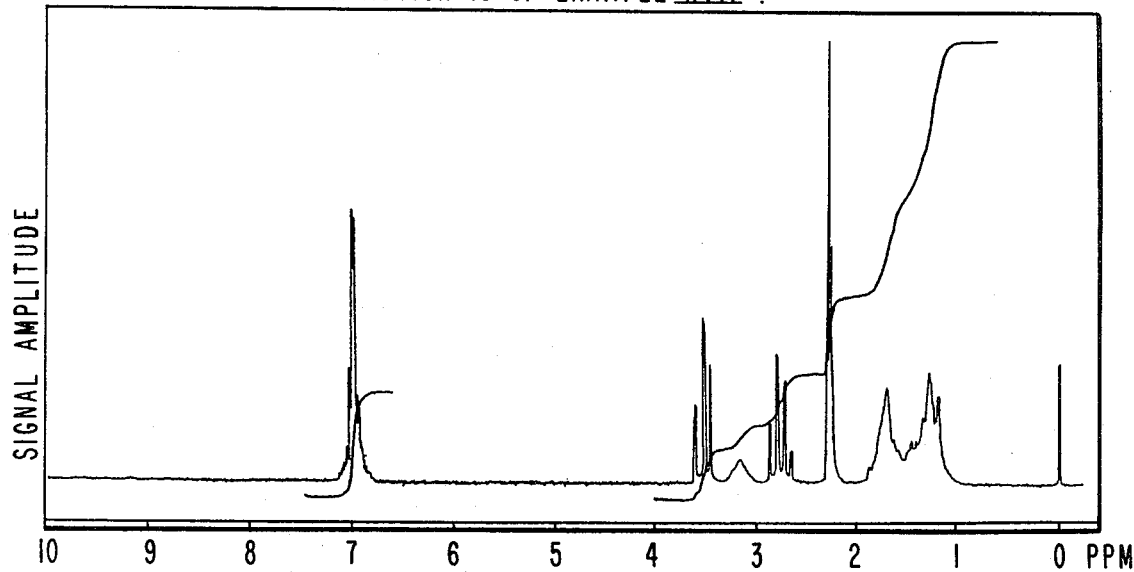
NMR SPECTRUM FOR FRACTION 10 OF EXAMPLE XVII.
FIG.11

IR SPECTRUM FOR FRACTION 10 OF EXAMPLE XVII.

CYCLOHEXYL PHENETHYLETHER DERIVATIVES FOR COMBATTING TOBACCO BEETLES

This is a divisional of application Ser. No. 235,844, filed Feb. 19, 1981, now U.S. Pat. No. 4,324,923, which in turn, is a continuation-in-part of application for U.S. Letters Patent, Ser. No. 192,238, filed on Sept. 30, 1980, now U.S. Pat. No. 4,306,096.

BACKGROUND OF THE INVENTION

This invention relates to phenethyl cyclohexylether derivatives, a novel process for preparing same, and to the use thereof in combatting insects as a result of the discovery that such cyclohexyl phenethylether derivatives are tobacco beetle pheromones or ectohormones; and in addition to the use of such phenethyl cyclohexylether derivatives in augmenting or enhancing the aroma or perfumes, colognes and perfumed articles (e.g., solid or liquid anionic, cationic, nonionic or zwitterionic detergents, fabric softeners, fabric softener articles, hair conditioners, odorants and deodorants). Obviously then, the invention also relates to a pleasant smelling pheromone or ectohormone useful for combatting insects yet, at the same time, not repulsive to the individual or group of individuals applying the pheromone or ectohormone to the area where the insects are to be combatted.

Pheromones or ectohormones are secreted by insects as so called socially active ingredients, e.g., as sexual attractant or aggregation substance. The use of these pheromones or ectohormones is known to attract insects into certain small sections of a contaminated area, to concentrate them in this area and then to destroy the insects in any known way, e.g., mechanically, chemically or with insecticides. This method leads to a very economical and concentrated use of the actual insecticides, especially of insecticides which are ecologically dangerous, whereby the spraying of large parts of the contaminated area in any expensive way, e.g., by spraying insecticides with an aeroplane, is avoided.

No pheromones have been discovered up to the present time for use with *Lasioderma serricorne* (*F.*). Thus, the pheromones known up to the present time belong to a large variety of chemical substances and are, as a rule, effective only with respect to certain insects such as, for example, for use in combatting insects of the order coleoptera and the family scolytidae and platypodidae which beetles cause substantial damage to forests and to the wood of trees generally as taught in U.S. Pat. No. 3,927,207 issued on Dec. 16, 1975.

Another problem as yet unsolved by the prior art concerns the utilization, either in conjunction with or as pheromones or ectohormones for insect attractants, of fragrance imparting, augmenting or enhancing agents. Such fragrance imparting, augmenting or enhancing agents must be either identical to or, at the very least, compatible with the pheromones or ectohormones. Previously such pheromones or ectohormones having their own aroma profiles usually have an aroma profile which either was esthetically displeasing or, at the very best, incapable of covering or deodorizing the chemical-like sharp, abrasive aroma of the insecticides used aganst the insects.

An optimal solution to the foregoing problems would be to create, in one chemical, a pheromone or ectohormone; an insecticide; and an aroma augmenting or enhancing substance which is compatible with said pheromone or ectohormone and with said insecticide.

Notwithstanding the aforementioned pheromone or ectohormone properties and notwithstanding the aforementioned insecticide properties, chemical compounds which can provide dry green hyacinth-like, rose-like, fruity and galbanum-like aromas which are both rich and full bodied as well as long lasting are desirable in the art of perfumery. Many of the natural materials which provide such fragrances and contribute such desired nuances to perfumery compositions are high in cost, unattainable at times, vary in quality from one batch to another and/or are generally subject to the usual variations of natural products.

There is, accordingly, a continuing effort to find synthetic materials which will replace, enhance or augment the fragrance notes provided by natural essential oils or compositions thereof. Unfortunately, many of these synthetic materials either have the desired nuances only to a relatively small degree or else contribute undesirable or unwanted odor to the compositions. The search for materials which can provide more refined, more natural-like, long-lasting dry green hyacinth, rose, fruity and galbanum aromas have been difficult and relatively costly in the areas of both natural products and synthetic products.

Arctander in "Perfume and Flavor Chemicls (Aroma Chemicals)", Volume II, 1969 describes phenylethyl alcohol as having a rose aroma.

Phenethyl propionate has been disclosed in the Journal of Economic Entomology, 66, (5), 1973, and has been indicated by McGovern et al to be an attractant for *Popillia japonica Newman* (Japanese beetles) particularly in combination with eugenol. Indeed, in that same paper by McGovern et al, it is indicated that trans-2-hexenal, a well-known perfume ingredient, is also a Japanese beetle attractant. The phenethyl propionate has the structure:

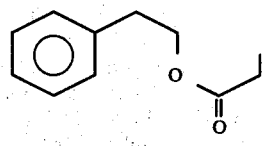

In another paper by McGovern et al, Journal of Economic Entomology, Volume 63, No. 1, page 276, it is indicated that methyl cyclohexanepropionate and certain related chemicals are also attractants for *Popillia japonica Newman*.

Research concerning *Lasioderma serricorne* (*F.*) and attractants therefor are limited to the use of extracts of natural food odors. Thus, the paper by Fletcher and Garrett entitled "Ovipositional Response of Three Strains of the Cigarette Beetle to Extracts of Food Odors" in Tobacco International, 182 (5(, pages 166–169, Mar. 7, 1980, Fletcher and Garrett disclose that the ovipositional response of three strains of the cigarette beetle is a function of different food odor attractants.

Nothing in the prior art, however, discloses the unexpected, unobvious and advantageous properties of the phenethyl cyclohexylethers having the generic structure:

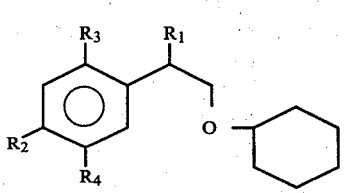

wherein $R_1$, $R_2$, $R_3$ and $R_4$ are the same or different and each represents methyl or hydrogen with the proviso that one of $R_2$, $R_3$ and $R_4$ is methyl and the other two of $R_2$, $R_3$ and $R_4$ are hydrogen; or processes for preparing same by reacting the phenethyl alcohol derivatives with cyclohexene. These compounds are not only useful per se for augmenting or enhancing the aroma of perfume compositions, colognes and perfumed articles but are also useful as *Lasioderma serricorne* (*F.*) pheromones and, in addition, as *Lasioderma serricorne* (*F.*) insecticides.

Ethers containing the phenylethyl moiety, however, are known in perfumery. Thus, Ishikawa et al, Japanese Kokai 77-07911 of Jan. 21, 1977 (abstracted in Chem. Abstracts 87:135063q) discloses the genus of compounds defined according to the structure:

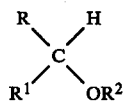

as being useful in perfumery; wherein R is alkyl; alkenyl; aryl; aralkyl; as well as cycloalkyl and $R^1$ is hydrogen or the same as R and $R^1$ is hydrogen or the same as R and $R^2$ is alkyl or phenyl alkyl. Furthermore, U.S. Pat. No. 3,734,970 (class 260 subclass 611A) discloses the use of the compound having the structure:

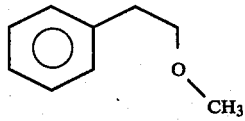

as being useful in augmenting or enhancing perfume aromas. It is indicated that this compound is prepared by reacting phenylethyl alcohol with an aluminum mercury couple to form the triphenyl ethoxy aluminum and the triphenyl ethoxy aluminum is then reacted with dimethoxy sulfoxide to produce the phenylethylmethylether. French Demande No. 2,373,276 of July 7, 1978 (abstracted in Chem. Abstracts 90:127414b(1979) discloses the compound having the structure:

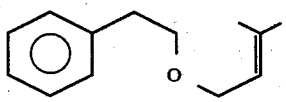

as being useful in augmenting or enhancing perfumes such as lilac perfumes.

BRIEF DESCRIPTION OF THE DRAWINGS

FIG. 1A is the GLC profile for the reaction product of Example IA at the end of the reaction and just prior to distillation.

FIG. 1B is the GLC profile for fraction 8 of the distillation product of the reaction product of Example IA which contains phenethyl cyclohexylether having the structure:

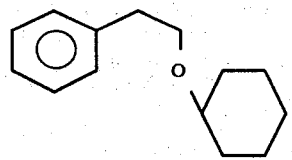

FIG. 1C is the GLC profile for fraction 10 of the distillation product of the reaction product of Example IA containing the compound having the structure:

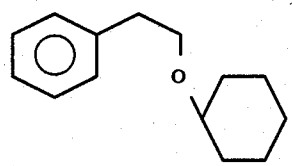

FIG. 1D is the GLC profile for fraction 12 of the distillation product of the reaction product of Example IA containing the compound having the structure:

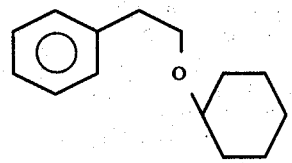

FIG. 2 is the NMR spectrum for peak "A" of the GLC profile of FIG. IA which consists of the compound having the structure:

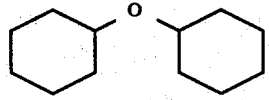

FIG. 3 is the NMR spectrum for peak "B" of the GLC profile of FIG. IA containing the compound having the structure:

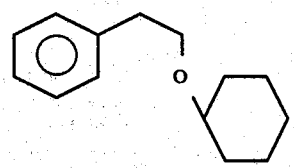

FIG. 4 is the infra-red spectrum for peak "B" of the GLC profile of FIG. IA containing the compound having the structure:

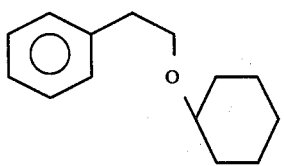

FIG. 5 is the GLC profile for the reaction product of Example IB containing the compound having the structure:

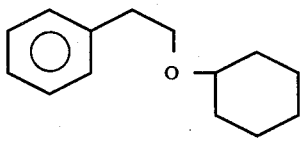

prior to distillation but subsequent to the sodium hydroxide wash of the reaction product.

FIG. 6A is the GLC profile for fraction 7 of the distillation product of the reaction product of Example IB containing the compound having the structure:

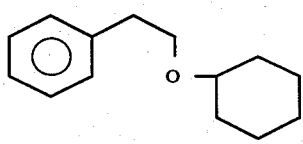

Figure 6B:
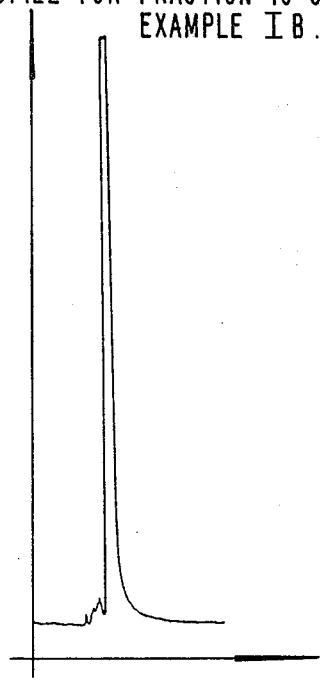

FIG. 6B is the GLC profile for fraction 10 of the distillation product of the reaction product of Example IB containing the compound having the structure:

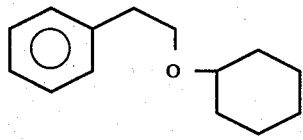

Figure 6C:
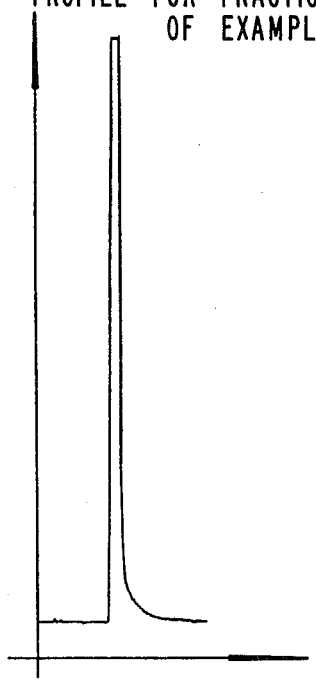

FIG. 6C is the GLC profile for fraction 22 of the distillation product of the reaction product of Example IB containing the compound having the structure:

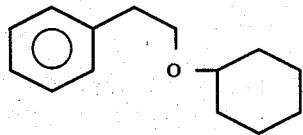

Figure 7A:
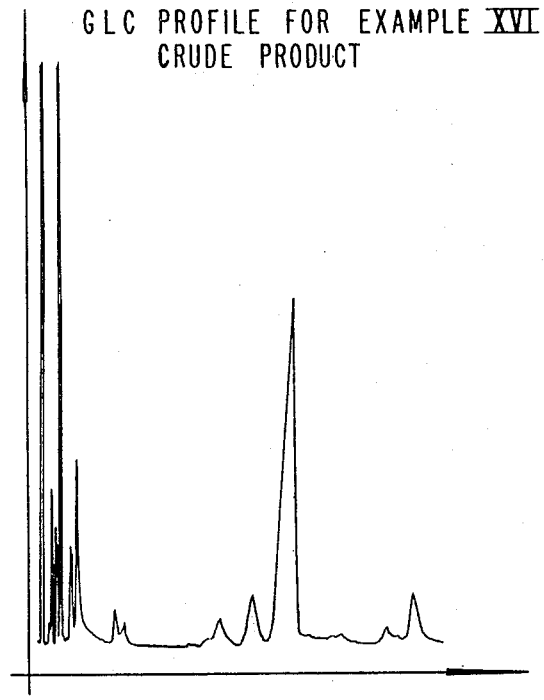

FIG. 7A is the GLC profile of the crude reaction product prior to distillation of Example XVI containing the compound having the structure:

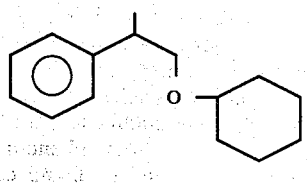

Figure 7B:
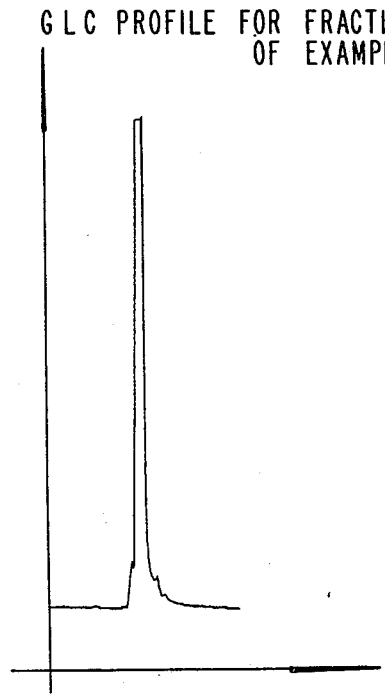

FIG. 7B is the GLC profile for fraction 8 of the distillation product of the reaction product of Example XVI containing the compound having the structure:

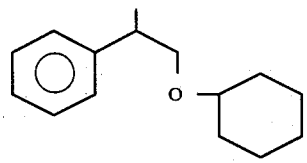

FIG. 8 is the NMR spectrum for fraction 6 of the distillation product of the reaction product of Example XVI containing the compound having the structure:

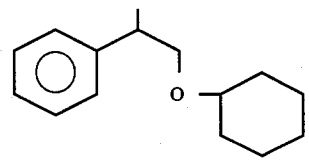

FIG. 9 is the infra-red spectrum for fraction 6 of the distillation product of the reaction product of Example XVI containing the compound having the structure:

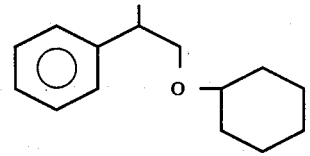

FIG. 10A is the GLC profile for the crude reaction product prior to distillation of Example XVII containing the compound having the structure:

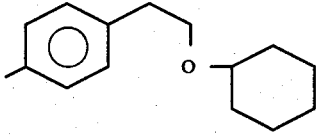

FIG. 10B is the GLC profile for fraction 8 of the distillation product of the reaction product of Example XVII containing the compound having the structure:

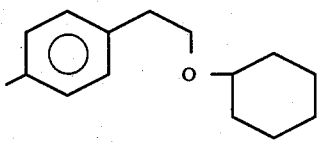

FIG. 11 is the NMR spectrum for fraction 10 of the distillation product of the reaction product of Example XVII containing the compound having the structure:

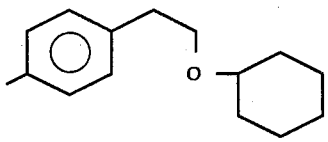

Figure 12:
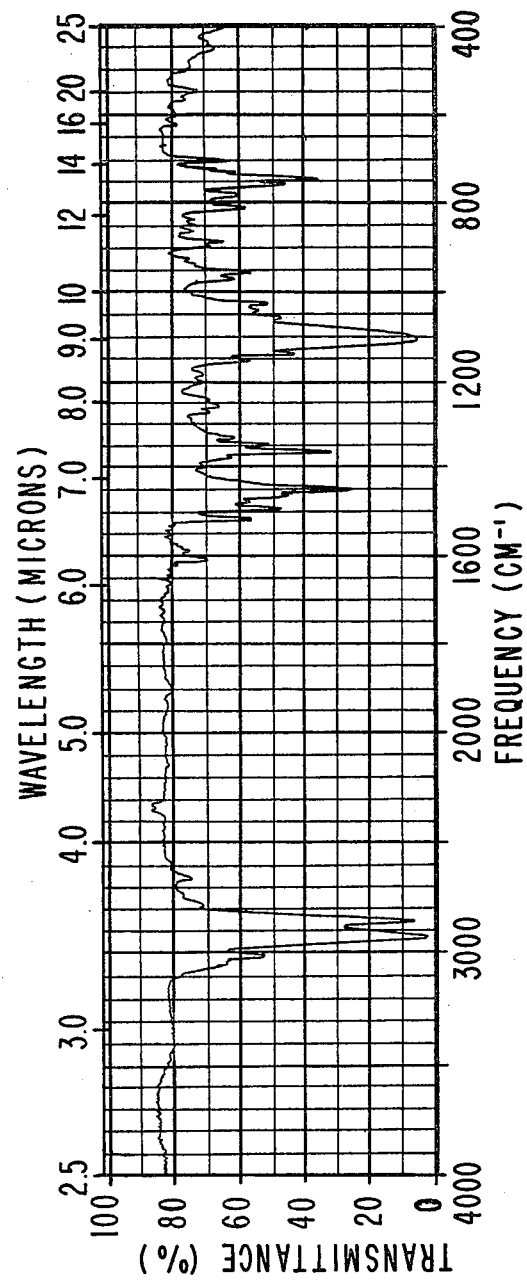

FIG. 12 is the infra-red spectrum for fraction 10 of the distillation product of the reaction product of Example XVII containing the compound having the structure:

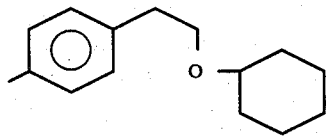

DETAILED DESCRIPTION OF FIG. 5

FIG. 5 is the GLC profile for the reaction product of Example IB resulting from the reaction of cyclohexene and phenylethyl alcohol.

The peak designated by the numeral "1" is the peak indicating unreacted cyclohexene.

The peak designated by the numeral "2" in the GLC profile is the peak which represents phenylethyl alcohol.

The peak designated by the numeral "3" represents the peak for the reaction product of Example IB, cyclohexyl phenethylether.

The conditions for this GLC profile obtention are 220° C. isothermal using a ⅛"×10' 10% SE-30 column.

THE INVENTION

The present invention proposes the use of cyclohexyl penethylether derivatives defined according to the structure:

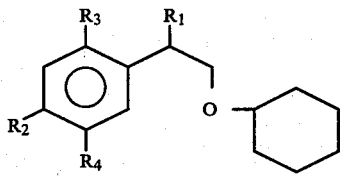

wherein $R_1$, $R_2$, $R_3$ and $R_4$ are the same or different and each represents methyl or hydrogen with the proviso that one of $R_2$, $R_3$ and $R_4$ is methyl and the other two of $R_2$, $R_3$ and $R_4$ are hydrogen, for combatting beetles of the order *Lasioderma serricorne* (*F.*) in such a manner that one or more of said cyclohexyl phenethylether derivatives not only act as a pheromone or ectohormone but also act as aroma augmenting or enhancing agents and, in addition, act as insecticides. Notwithstanding the pheromone and insecticide properties of said cyclohexyl phenethylether derivatives, the instant invention also provides cyclohexyl phenethylether derivatives as fragrances capable of augmenting or enhancing the fragrance of perfume compositions, colognes and perfumed articles (e.g., solid or liquid anionic, cationic, nonionic or zwitterionic detergents, fabric softeners, dryer-added fabric softener articles, hair conditioners, deodorants and cosmetic powders). The present invention also proposes a new process for preparing said cyclohexyl phenethylether derivatives according to the reaction:

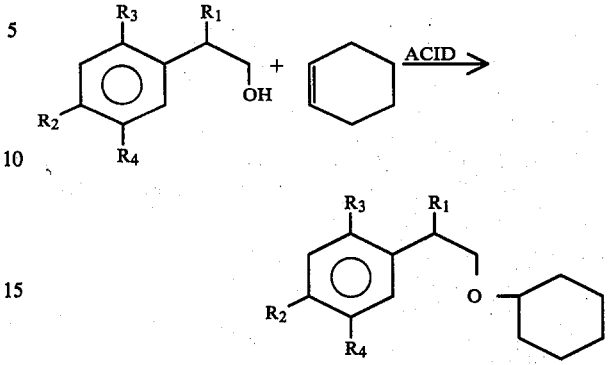

wherein $R_1$, $R_2$, $R_3$ and $R_4$ are the same or different and each represents methyl or hydrogen with the proviso that one of $R_2$, $R_3$ and $R_4$ is methyl and the other two of $R_2$, $R_3$ and $R_4$ are hydrogen, which reaction is carried out under specific conditions as indicated, infra.

The cyclohexyl phenethylether derivatives of our invention are capable of augmenting or enhancing the dry green, hyacinth, rose, fruity and galbanum aromas of perfumes, perfumed articles and colognes of our invention. Of course, as part of the perfumed articles of our invention, there are the "perfumed insecticide-pheromone" compositions of our invention.

The destruction of the *Lasioderma serricorne* (*F.*) insects can be achieved by distributing the cyclohexyl phenethylether or pheromonal attractants in the contaminated area at separate individual places, namely, by means of catch trees. These are impregnated with the attractants which may, if desired, act as insecticides too; or one or more of the cyclohexyl phenethylether derivatives may be augmented by one or more additional insecticides whereupon the catch trees are sprayed with another insecticide either before or after the insects have gathered at the catch tree (whatever insects are still alive after contact with said cyclohexyl phenethylether derivatives). Instead of using one or more cyclohexyl phenethylether derivatives taken alone or taken together with another insecticide, one may also use a chemical sterilizing compound. Further, the catch tree may be treated with other chemicals which can be burned. Another possible method for destroying insects with one or more of the cyclohexyl phenethylether derivatives of our invention makes use of the disturbance or perturbance theory. Instead of physically destroying the insects with either high concentrations of one or more of the cyclohexyl phenethylether derivatives of our invention or by using one or more of the cyclohexyl phenethylethers of our invention followed by additional insecticide, it is also possible to combine one or more of the cyclohexyl phenethylether derivatives of our invention physically with one or more additional stronger insecticides before using. Thus, it is possible now to spray a combination of one or more cyclohexyl phenethylethers which have pleasant aromas in combination with insecticides whose original aroma(s) are covered using one or more of the cyclohexyl phenethylether(s) in certain centrally located areas or in the form of rows in the contaminated area. Furthermore, one or more of the cyclohexyl phenethylethers can be mixed with the usual solid or liquid carriers or with biocides such as stronger insecticides, pesticides or herbicides. The mixture may contain surface active agents to obtain a better distribution or adherence to the plants.

The cyclohexyl phenethylether derivatives of our invention may be prepared according to a conventional method by reacting cyclohexanol with beta phenylethyl alcohol derivatives such as beta phenylethyl alcohol in the presence of an acid such as sulfuric acid according to the reaction:

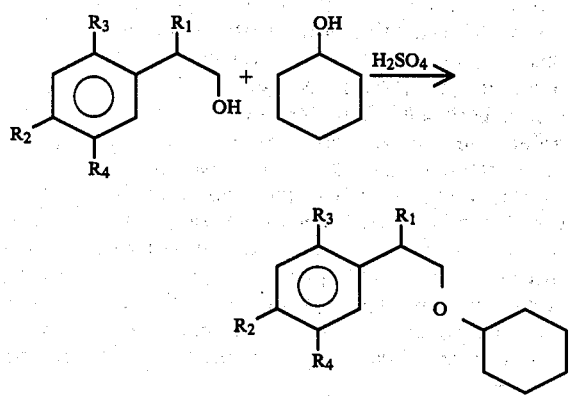

wherein $R_1$, $R_2$, $R_3$ and $R_4$ are the same or different and each represents methyl or hydrogen with the proviso that one of $R_2$, $R_3$ and $R_4$ is methyl and the other two of $R_2$, $R_3$ and $R_4$ are hydrogen. Thus, for example, the reaction:

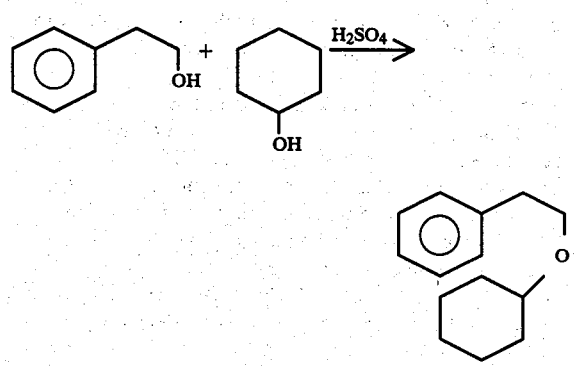

is typical of such a reaction. Alternatively, an alkali metal phenethyl alcoholate derivative may be reacted with a cyclohexyl halide such as cyclohexyl bromide or cyclohexyl chloride or an alkali metal cyclohexyl alcoholate may be reacted with beta phenylethyl chloride or beta phenylethyl bromide by means of a "Williamson" synthesis, conventional in the organic chemistry art.

However, more efficiently and of lower cost is the carrying out of a process of reacting a beta phenylethyl alcohol derivative with cyclohexene in the presence of specific acid catalysts under specific conditions according to the reaction:

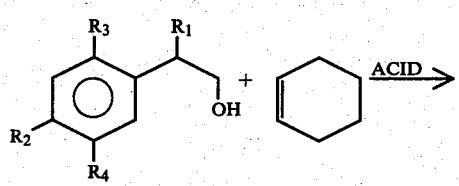

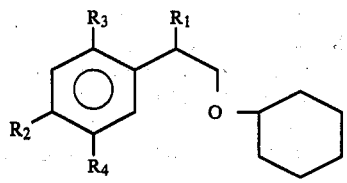

wherein $R_1$, $R_2$, $R_3$ and $R_4$ are the same or different and each represents methyl or hydrogen with the proviso that one of $R_2$, $R_3$ and $R_4$ is methyl and the other two of $R_2$, $R_3$ and $R_4$ are hydrogen.

The temperature of reaction may vary from 90° C. up to about 180° C. at from 1 atmosphere pressure up to 100 atmospheres pressure. Higher temperatures of reaction require higher pressures of reaction.

The mole ratio of phenylethyl alcohol derivative to cyclohexene may vary from 1:1 up to about 1:2.

Various acid catalysts can be used including mineral acids such as sulfuric acid or methane sulfonic acid or paratoluene sulfonic acid; or the acid catalyst may be a solid acid catalyst such as a sulfonated copolymer of styrene and divinyl benzene (e.g., "Amberlyst ® 15" manufactured by the Rohm & Haas Corporation of Philadelphia, Pennsylvania) or an acid clay such as an activated clay adsorbent such as Filtrol ® 105 having the following properties:

Particle size analysis:
  By Roller (10 liters/min. air rate)
    0-5 Microns, Wt. %—8
    0-20 Microns, wt. %—43
  By Taylor Standard Sieve
    Through 100 Mesh, wt. %—100
    Through 200 Mesh, wt. %—95
    Through 325 Mesh, wt. %—78
Apparent Bulk densiity, lb/cu. ft.: 42
Free moisture, wt. %: 15
Free and Combined moisture, wt. % (loss at 1700° F.): 21
Surface area (BET Method), Sq.M/gm.: 300
Acidity, phenolphthalein, mg.KOH/gm.: 4.8
Filter rate, cc/min.: 38
Oil retention, wt. %: 35

The weight ratio of acid catalyst to phenylethyl alcohol derivative may vary from about 2 wt. % up to about 20 wt. %.

The time of reaction is primarily a function of four variables:
  1. temperature of reaction
  2. conversion desired
  3. particular acid catalyst utilized and
  4. concentration of acid catalyst in the reaction mass In general, higher temperatures of reaction give rise to a shorter required time of reaction, but too high a temperature of reaction (e.g., greater than about 180° C.) and/or too long a time of reaction causes a diminution of conversion due to product decomposition. In general, higher concentration of acid catalyst in the reaction mass gives rise to shorter time periods of reaction for a given conversion to the desired cyclohexyl phenethylether derivative. Thus, in general, a time of reaction may vary from about 1 hour up to about 48 hours.

Notwithstanding the pheromonal and insecticidal activity of the cyclohexyl phenethylether derivatives of our invention, the cyclohexyl phenethylethers of our invention can be used to contribute long lasting dry green, hyacinth, rose, fruity and galbanum aromas which are unexpectedly full and rich for a very long period of time to perfumes, perfumed articles and colognes. As olfactory agents, the cyclohexyl phenethylether derivatives of our invention can be formulated into or used as components as a "perfume composition" or can be used as components of a "perfumed article" or the perfume composition may be added to "perfumed articles".

Examples of the compounds prepared according to the process of our invention, the phenylethyl alcohol derivative reactant for producing such compound and the olfactory properties of such compound are set forth in Table I below:

TABLE I

| Product Structure | Reactant | Olfactory Properties |
|---|---|---|
| 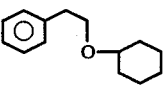 |  | A long lasting dry green, hyacinth, rose and galbanum aroma. |
| 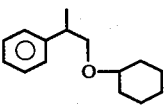 |  | A floral, green, galbanum-like aroma. |
| 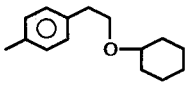 |  | An interesting low keyed burnt fruity aroma. |

The term "perfume composition" is used herein to mean a mixture of organic compounds including, for example, alcohols, aldehydes, ketones, nitriles, ethers in addition to and other than the cyclohexyl phenethylether derivatives of our invention, lactones, natural essential oils, synthetic essential oils and frequently hydrocarbons which are admixed so that the combined odors of the individual components produce a pleasant or desired fragrance. Such perfume compositions usually contain: (a) the main note or the "bouquet" or foundation stone of the composition (b) modifiers which round off and accompany the main note; (c) fixatures which include odorous substances which lend a particular note to the perfume throughout all stages of evaporation, and substances which retard evaporation; and (d) top notes which are usually low-boiling, fresh-smelling materials.

In perfume compositions, the individual component will contribute its particular olfactory characteristics, but the overall effect of the perfume composition will be the sum of the effects of each of the ingredients. Thus, the cyclohexyl phenethylether derivatives of our invention can be used individually or in combination to alter the aroma characteristics of a perfume composition, for example, by highlighting or moderating the olfactory reaction contributed by another ingredient in the composition.

The amount of one or more of the cyclohexyl phenethylether derivatives of our invention which will be effective in perfume compositions depends upon many factors including the other ingredients, their amounts and the effects which are desired. It has been found that perfume compositions containing as little as 0.05% of one or a mixture of the cyclohexyl phenethylether derivatives of our invention or even less can be used to impart long lasting, interesting, very strong, dry green, hyacinth, rose, fruity and galbanum aromas to soaps, liquid and solid cationic, nonionic, anionic and zwitterionic detergents, cosmetic powders, liquid and solid fabric softeners, dryer-added fabric softener articles, optical brightener compositions and other products. The amount employed can range up to 50% or more and will depend upon considerations of cost, nature of the end product and the effect desired on the finished product and particular fragrance sought.

One or more of the cyclohexyl phenethylether derivatives of our invention can be used alone or in combination with one another or in a perfume composition as an olfactory component in detergents and soaps, space odorants and deodorants; perfumes; colognes, toilet water; bath salts, hair preparations such as lacquers, brilliantines, pomades and shampoos; cosmetic preparations such as creams, deodorants, hand lotions and sun screens; powders such as talcs, dusting powders, face powder and the like. When used as an olfactory component of a perfumed article, as little as 0.01% of one or a mixture of cyclohexyl phenethylether derivatives will suffice to impart an interesting long lasting dry green, hyacinth, rose, fruity and/or galbanum aroma. Generally no more than 0.5% is required in the perfumed article.

In addition, the perfume composition can contain a vehicle or carrier for the cyclohexyl phenethylether derivatives taken alone or taken in combination with other ingredients. The vehicle can be a liquid such as an alcohol such as ethanol, a glycol such as propylene glycol, or the like. The carrier can be an absorbent solid such as a gum or components for encapsulating the composition such as gelatin which can be used to form a capsule wall surrounding the perfume oil by means of coacervation.

It will thus be apparent that one or more of the cyclohexyl phenethylether derivatives of our invention can be utilized to alter, modify, augment or enhance the aroma of a wide variety of consumable materials including fragrance formulations, colognes, pheromones, insecticides and perfumed articles in general.

The following examples serve to illustrate our invention and this invention is to be considered restricted thereto only as indicated in the appended claims.

All parts and percentages given herein are by weight unless otherwise specified.

EXAMPLE IA

PREPARATION OF CYCLOHEXYL PHENETHYLETHER

Reaction:

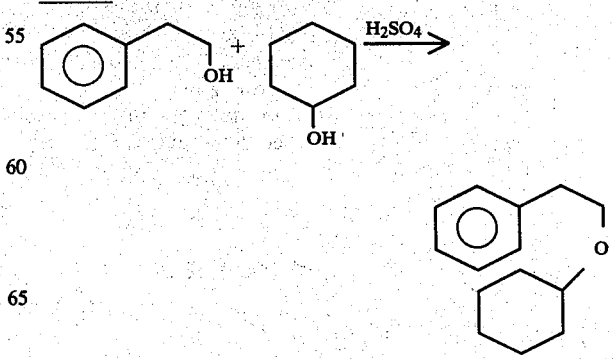

Into a 2 liter reaction vessel equipped with stirrer, thermometer, heating mantle and overhead condenser with azeotrope takeoff apparatus is placed 488 grams of betaphenylethyl alcohol; 440 grams of cyclohexanol and 100 grams of concentrated sulfuric acid. The reaction mass is then heated to a temperature of 115° C. and maintained at a temperature in the range of 104°–127° C. at reflux while azeotropically removing 80 ml water, for a period of 3 hours. At the end of the 3 hour period, a sample is analyzed by means of GLC analysis (conditions: 180° C. isothermal using an SE-30 packed column). FIG. 1A is the GLC profile of the reaction product at this point.

The resulting reaction mass is then distilled on a 1'×29/42 distillation column yielding the following fractions:

| Fraction Number | Vapor Temp. °C. | Liquid Temp. °C. | Vacuum mm. Hg pressure | Reflux Ratio R/D |
|---|---|---|---|---|
| 1 | 27 | 40 | 1.2 | 1/4 |
| 2 | 70 | 100 | 1.0 | 4/1 |
| 3 | 67 | 100 | 1.0 | 4/1 |
| 4 | 67 | 100 |  | 4/1 |
| 5 | 70 | 105 | 0.7 | 4/1 |
| 6 |  |  |  | 4/1 |
| 7 | 70 | 130 | 0.7 | 4/1 |
| 8 | 88 | 140 |  | 4/1 |
| 9 | 100 | 132 | 0.55 | 4/1 |
| 10 | 100 | 160 |  | 4/1 |
| 11 | 100 | 165 |  | 4/1 |
| 12 | 102 | 185 | 0.4 | 4/1 |
| 13 | 107 | 205 | 0.5 | 4/1 |

FIG. 1B is the GLC profile for fraction 8 of the distillation product of the reaction product of this example which contains phenethyl cyclohexylether having the structure:

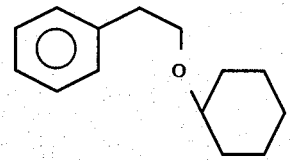

FIG. 1C is the GLC profile for fraction 10 of the distillation product of the reaction product of this example containing the compound having the structure:

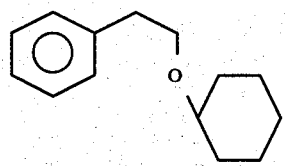

FIG. 1D is the GLC profile for fraction 12 of the distillation product of the reaction product of this example containing the compound having the structure:

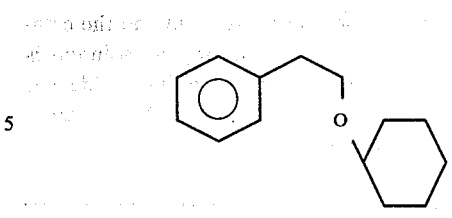

FIG. 2 is the NMR spectrum for peak "A" of the GLC profile of FIG. 1A which consists of the compound having the structure:

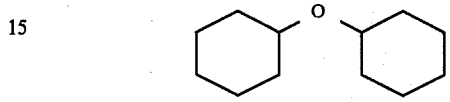

FIG. 3 is the NMR spectrum for peak "B" of the GLC profile of FIG. 1A containing the compound having the structure:

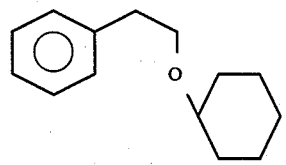

FIG. 4 is the infra-red spectrum for peak "B" of the GLC profile of FIG. 1A containing the compound having the structure:

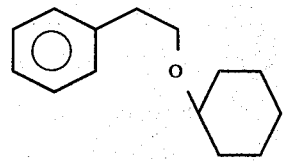

EXAMPLE IB

Reaction:

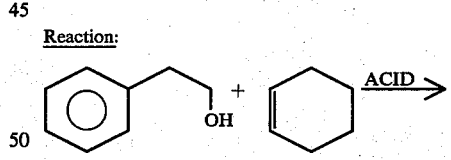

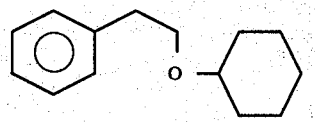

Phenethyl alcohol (1487 grams; 12.2 moles) and Amberlyst 15 ® catalyst (a sulfonated phenyl polyethylene ion exchange resin manufactured by the Rohm & Haas Corporation of Philadelphia, Pa. (85.4 grams)) are heated to 110° C. 1000 grams (12.2 moles) of cyclohexene is added dropwise to the reaction mass over a period of 4.5 hours while maintaining the reaction mass at 110° C. During the addition of the cyclohexene, residual water (22 ml) is removed by azeotropic distillation through a water separating trap. The reaction mass is stirred at 110° C. for an additional 5.25 hours. At this point in time, the reaction mass is cooled and the catalyst is removed by filtration. The organic solution is washed with 400 grams of 30% sodium hydroxide and then distilled through a 1½"×12" Goodloe column yielding the following fractions:

| Fraction Number | Vapor Temp. (°C.) | Liquid Temp. (°C.) | Head Vac. mm/Hg. Pressure | Reflux Ratio | Weight of Fraction |
| --- | --- | --- | --- | --- | --- |
| 1 | 35/30 | 75/130 | 300 | 100 | 236.7 |
| 2 | 25/74 | 121/105 | 3 | 9:1 | 77g |
| 3 | 71 | 96 | 5.8 | 9:1 | 35.4 |
| 4 | 72 | 121 | 3.0 | 9:1 | 120.9 |
| 5 | 74 | 137 | 3.0 | 9:1 | 225.9 |
| 6 | 105 | 140 | 3.0 | 9:1 | 61.9 |
| 7 | 105 | 140 | 3.0 | 9:1 | 44.1 |
| 8 | 105 | 140 | 3.0 | 9:1 | 34.2 |
| 9 | 105 | 140 | 3.0 | 9:1 | 113g |
| 10 | 105 | 142 | 2.6 | 1:1 | 82g |
| 11 | 105 | 145 | 2.6 | 1:1 | 101.7 |
| 12 | 105 | 145 | 2.6 | 1:1 | 83g |
| 13 | 105 | 139 | 2.6 | 1:1 | 92.7 |
| 14 | 105 | 140 | 2.6 | 1:1 | 116.3 |
| 15 | 105 | 140 | 2.6 | 1:1 | 84.7 |
| 16 | 105 | 137 | 2.6 | 1:1 | 100.8 |
| 17 | 105 | 138 | 2.6 | 1:1 | 107.3 |
| 18 | 105 | 140 | 2.6 | 1:1 | 90.8 |
| 19 | 105 | 142 | 2.6 | 1:1 | 97g |
| 20 | 108 | 146 | 3mm | 9:1 | 820g |
| 21 | 108 | 157 | 3 | 9:1 | 111.5 |
| 22 | 108 | 163 | 3 | 9:1 | 79g |
| 23 | 117 | 199 | 3 | 9:1 | 54.4 |
| 24 | 129 | 250 | 3 | 9:1 | 95.1 |

Fractions 11–22 contain phenylethyl cyclohexyl ether having a purity of greater than 99%.

FIG. 5 is the GLC profile for the reaction product immediately after the sodium hydroxide wash and prior to distillation.

FIG. 6A is the GLC profile for fraction 7 of the distillation product of the reaction product of Example IB containing the compound having the structure:

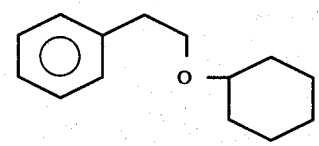

FIG. 6B is the GLC profile for fraction 10 of the distillation product of the reaction product of Example IB containing the compound having the structure:

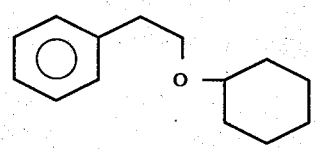

FIG. 6C is the GLC profile for fraction 22 of the distillation product of the reaction product of Example IB containing the compound having the structure:

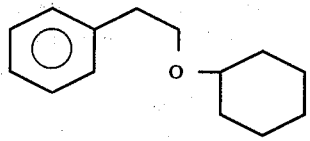

EXAMPLE II

Field tests are made each time using 100 male and 100 female *Lasioderma serricorne* (*F.*) cigarette beetles. The beetles were released at a certain distance from the source of attraction which was treated with cyclohexyl phenethylether prepared according to either of Example IA or IB. Further, felled trees having already been contaminated with the respective beetles are positioned at both sides of the starting point. After a certain period of time the amount of insects gathered at the source of attraction was determined thus indicating the effectiveness of the pheromonal mixture according to the invention.

Field tests with *Lasioderma serricorne* (*F.*) are made whereby the distance between the starting point and the source of attraction is 50 meters. Four independent field tests were made whereby 42% of the male beetles and 46% of the female beetles gathered at each catch tree. The concentration of insects at the catch tree was 55% of the male insects and 58% of the female insects. In all these tests the catch tree was impregnated with a 0.7% ethanolic solution of cyclohexyl phenethylether (7 gm cyclohexyl phenethylether per 92 gm of 95% aqueous ethanol).

EXAMPLE III

During two consecutive days several felled oak trees surrounding a field of tobacco plants were treated with 250 mg of phenethyl cyclohexylether in 1.0% ethanolic solution. These trees were exposed in an area which were contaminated with *Lasioderma serricorne* (*F.*). After 3 to 4 days 100 beetles per square meter were observed on the logs. Other untreated logs or trees in the direct neighborhood of the treated logs or trees showed very few (about 12) insects per square meter on the average while other trees at a distance of 10 to 20 meters showed no contamination.

EXAMPLE IV

In a large test field, mixtures of cyclohexyl phenethylether in admixture with different DDT preparations, fluorine-containing mixtures and arsenic-containing mixtures as well as hexachloro-cyclohexane were used. These mixtures contained also small amounts of surface-active agents and carriers. The mixtures were applied to catch trees namely logs of oak trees in an area of tobacco plants contaminated with *Lasioderma serricorne* (*F.*). The distance between the catch trees was always 200 meters. After 8 days there was no contamination either in the tobacco fields or around the oak trees. About 92% of the *Lasioderma serricorne* (*F.*) insects were destroyed. Surprisingly, it was found that after the fourth day the attracting effect was not diminished in spite of dead insects being present. Furthermore, in those areas where cyclohexyl phenethylether was used alone, the average number of insects destroyed was about 80% which in itself is surprising. Thus, the cyclohexyl phenethylether not only acts as a pheromone but also as an insecticide. Furthermore, the entire area wherein the cyclohexyl phenethylether was used had a faint pleasant floral aroma covering any adverse and esthetically displeasing aroma of any other insecticides that were used.

EXAMPLE V

The following mixture is prepared:

| Ingredients | Parts by Weight |
| --- | --- |
| Phenylacetic acid | 70.0 |
| Coumarin | 20.0 |
| Phenylethylphenyl acetate | 100.0 |
| Phenyl ethyl alcohol | 5.0 |
| Benzyl benzoate | 100.0 |
| Dimethylphenylethyl carbinol | 10.0 |
| Methyl anthranilate | 5.0 |
| Beta ionone | 10.0 |
| Cyclohexyl phenethylether | 30.0 |

The cyclohexyl phenethylether prepared according to either of Example IA or IB imparts the dry green hyacinth, rose, galbanum-like aroma to this honey fragrance while giving it a very warm undertone and imparting a very long lasting floral top note to this fragrance.

EXAMPLE VI

PREPARATION OF A COSMETIC POWDER COMPOSITION

A cosmetic powder is prepared by mixing in a ball mill 100 grams of talcum powder with 0.25 grams of the perfume composition prepared according to Example V. It has an excellent floral aroma.

EXAMPLE VII

PERFUMED LIQUID DETERGENT

Concentrated liquid detergents (Lysine salt of n-dodecylbenzene sulfonic acid as more specifically described in U.S. Pat. No. 3,948,818 issued on Apr. 6, 1976) with floral aroma nuances and rose, galbanum and hyacinth-like top notes are prepared containing 0.10%, 0.15% and 0.20% of the fragrance prepared according to Example V. They are prepared by adding and homogeneously mixing the appropriate quantity of fragrance formulation prepared according to Example V in the liquid detergent. The detergents all possess excellent floral aromas with dry green hyacinth, rose and galbanum nuances, the intensity increasing with greater concentrations of perfume composition prepared according to Example V.

EXAMPLE VIII

PREPARATION OF A COLOGNE AND HANDKERCHIEF PERFUME

The composition prepared according to Example V is incorporated into a cologne at concentrations of 2.0%, 2.5%, 3.0%, 4.0%, 4.5% and 5.0% in 80%, 85%, 90% and 95% aqueous food grade ethanol; and into handkerchief perfumes at concentrations of 15%, 20% and 30% (in 80%, 85% and 95% aqueous food grade ethanol). A distinctive and definitive dry green hyacinth, rose, galbanum, rich and full-bodied floral aroma is imparted to the cologne and to the handkerchief perfume at all levels indicated.

EXAMPLE IX

PREPARATION OF SOAP COMPOSITION 100 grams of soap chips are mixed with 1 gram of the formulation of Example V until a homogeneous composition is obtained. The homogeneous composition is heated under three atmospheres pressure at 180° C. for a period of three hours and the resulting liquid is placed into soap molds. The resulting soap cakes, on cooling, manifest excellent floral aromas with dry green hyacinth, rose and galbanum nuances that are very long lasting.

EXAMPLE X

PREPARATION OF A SOLID DETERGENT COMPOSITION

A detergent is prepared from the following ingredients according to Example I of Canadian Pat. No. 1,007,948:

| | Percent by Weight |
| --- | --- |
| "Neodol 45-11" (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate free" detergent. A total of 100 grams of this detergent is admixed with 0.15 grams of the honey based perfume of Example V. Each of the detergent samples have an excellent floral honey-like, dry green hyacinth, rose and galbanum aroma.

EXAMPLE XI

DRYER-ADDED FABRIC SOFTENER ARTICLE

Utilizing the procedure of Example I at column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:
1. a water "dissolvable" paper ("Dissolvo Paper");
2. Adogen 448 (m.p. about 140° F.) as the substrate coating; and
3. an outer coating having the following formulation (m.p. about 150° F.):
   57% $C_{20-22}$ HAPS
   22% isopropyl alcohol
   20% antistatic agent
   1% of cyclohexyl phenethylether produced according to either of Example IA or IB A fabric softening composition prepared as set forth above having a dry green hyacinth, rose, galbanum and generally floral aroma characteristic consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. A pleasant floral aroma is imparted in a pleasant manner to the head space in the dryer on operation thereof using the said dryer-added fabric softening nonwoven fabric.

EXAMPLE XII

A liquid detergent composition prepared according to Example IV of United Kingdom Pat. No. 1,498,520 whereby the following ingredients are admixed:

| Ingredient | Weight % |
|---|---|
| Coconut alcohol ethoxylate | 30% |
| Linear alkyl benzene sulfonate, triethanolamine salt (alkyl = $C_{11.8}$avg.) | 10% |
| Potassium chloride | 3% |
| Triethanolamine | 3% |
| Triethanolammonium citrate | 2% |
| Ethyl alcohol | 5% |
| Soil release ether "D" | 1.0% |
| Cyclohexyl phenethylether prepared according to either of Example IA or IB | 3.0% |
| Water | Balance |

The soil release ether "D" is defined according to Table II on page 15 of United Kingdom Pat. No. 1,498,520.

This composition is prepared by admixing all of the ingredients exclusive of soil release ether "D" and agitating the mixture until all electrolytes are dissolved. Soil release ether "D" is then admixed with the solution in the form of a dry powder which passes through a 150 mesh standard sieve. The resulting composition is in the liquid state and is easily pourable. The composition is found not to redden on contact with plastic bottles, does not gel when diluted with water and has a long-lasting aroma which can be described as dry green hyacinth, rose, galbanum and rich and rather long lasting. Indeed, the aroma lasts for several weeks when exposed to the atmosphere.

This composition is added to an aqueous laundrying bath at a concentration of 0.20% (weight) at a temperature of 55° C., water hardness 7 grains per gallon and a pH of 10.0. Polyester and mixed polyester/cotton fabrics are laundered in the bath for a period of 10 minutes after which the fabrics are thoroughly rinsed with fresh water and dried at ambient temperatures. The fabrics are provided with a soil release finish. The head space above the fabrics has a pleasant faint aroma which can be described as hyacinth, rose, and galbanum and also rather long-lasting (about 3 days).

EXAMPLE XIII

PREPARATION OF A COSMETIC POWDER COMPOSITION

A cosmetic powder is prepared by admixing in a ball mill, 100 grams of talcum powder with 0.25 grams of phenethyl cyclohexylether prepared according to either of Example IA or IB. The resulting cosmetic powder has an excellent dry green hyacinth, rose, galbanum, rich and full-bodied floral fragrance which is very long-lasting.

EXAMPLE XIV

PERFUMED LIQUID DETERGENT

Concentrated liquid detergents (Lysine salt of n-dodecylbenzene sulfonic acid as more specifically described in U.S. Pat. No. 3,948,818 issued on Apr. 6, 1976) with dry green hyacinth, rose, galbanum rich and full-bodied floral aroma are prepared containing 0.10%, 0.15%, 0.20% and 0.25% of cyclohexyl phenethylether prepared according to either of Example IA or IB. They are prepared by adding and homogeneously admixing the appropriate quantity of phenethyl cyclohexylether in the liquid detergent. The detergents all possess intense long-lasting dry green hyacinth, rose, galbanum and generally floral aroma characteristics.

EXAMPLE XV

PREPARATION OF COLOGNES AND HANDKERCHIEF PERFUMES

Cyclohexyl phenethylether prepared according to either of Example IA or IB is incorporated into colognes at concentrations of 2.0%, 2.5%, 3.0%, 3.5%, 4.0% and 4.5% in 80%, 85%, 90% and 95% aqueous food grade ethanol; and into handkerchief perfumes at concentrations of 15%, 20%, 25% and 30% (in 80%, 90% and 95% aqueous ethanol). Distinctive dry green hyacinth, rose, galbanum, rich and full-bodied floral aroma nuances which are very long-lasting on dry-out (54 hours) are imparted to the colognes and to the handkerchief perfumes at the various above levels indicated.

EXAMPLE XVI

PREPARATION OF CYCLOHEXYL HYDROTROPYL ETHER

Reaction:

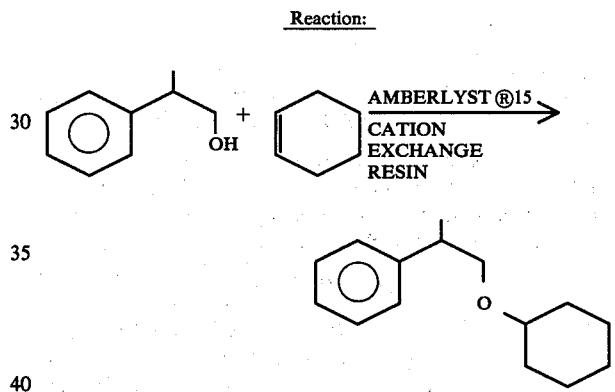

Into a stirred slurry of 408 grams of betamethylphenylethyl alcohol and 25 grams of Amberlyst ® 15 (a polysulfonated polystyrene cation exchange resin manufactured by the Rohm & Haas Company of Philadelphia, Pa.) maintained at 110° C. is added 246 grams of cyclohexene over a 2.75 hour period. The reaction mass is aged at 110° C. for an additional two hours whereupon it is cooled and filtered. The solution is then heated at reflux with 80 grams of 30% aqueous sodium hydroxide. The reaction mass is then cooled and washed with one liter of water. The organic layer is then separated from the aqueous layer and distilled and fractions rich in product are then fractionated through a 12"×1" Goodloe packed column to yield the following fractions:

| Fraction Number | Vapor Temp. (°C.) | Liquid Temp. (°C.) | mm/Hg. Pressure | Reflux Ratio | Weight of Fraction |
|---|---|---|---|---|---|
| 1 | 47/92 | 110/RO | 1.4 | 9:1 | |
| 2 | 85 | 125 | 1.4 | 9:1 | 17g |
| 3 | 85 | 124 | 1.4 | 9:1 | 18g |
| 4 | 85 | 124 | 1.4 | 3:1 | 24.5 |
| 5 | 97 | 119 | 1.4 | 2:1 | 31.5 |
| 6 | 87 | 125 | 1.4 | 2:1 | 31.6 |
| 7 | 93 | 127 | 1.4 | 2:1 | 27.5 |
| 8 | 86 | 129 | 1.2 | 2:1 | 21.6 |
| 9 | 86 | 136 | 1.2 | 2:1 | 22 |

-continued

| Fraction Number | Vapor Temp. (°C.) | Liquid Temp. (°C.) | mm/Hg. Pressure | Reflux Ratio | Weight of Fraction |
|---|---|---|---|---|---|
| 10 | 94 | 145 | 1.2 | 2:1 | 11.3 |
| 11 | 102 | 146 | 1.2 | 2:1 | 13.6 |
| 12 | 108 | 160 | 1.2 | 2:1 | 17.1 |
| 13 | 105 | 185 | 1.2 | 2:1 | 3.6g |

FIG. 7A is the GLC profile of the crude reaction product (conditions: ⅛"×10' 10% SE 30 packed column operated at 180° C. isothermal).

FIG. 7B is the GLC profile for fraction 8 of the distillation product (conditions: ⅛"×10' 10% SE 30 packed column; programmed at 220° C. isothermal).

FIG. 8 is the NMR spectrum for fraction 6 of the distillation product set forth above.

FIG. 9 is the infra-red spectrum for fraction 6 of the distillation product as set forth above.

The resulting product has a floral, green, galbanum-like fruity aroma.

EXAMPLE XVII

PREPARATION OF p-METHYL PHENYLETHYL CYCLOHEXYL ETHER

Reaction:

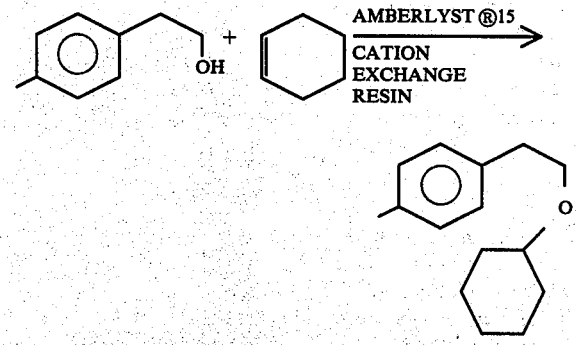

246 grams of cyclohexene is added to a stirred slurry of p-methyl phenyl beta ethanol (408 grams) and 25 grams of Amberlyst® 15 cation exchange resin maintained at 110° C., over a 2 hour period. The reaction mass is then aged at 110° C. for an additional 3 hours whereupon it is cooled and filtered. The resulting solution is then heated at reflux with 80 grams of 30% aqueous sodium hydroxide. The reaction mass is then cooled and the resulting organic layer is washed with 1 liter of water. The organic layer is separated from the reaction mass and distilled through a 1½"×12" Goodlow packed column to afford the following distillation fractions:

| Fraction Number | Vapor Temp. (°C.) | Liquid Temp. (°C.) | Pressure mm/Hg. | Reflux Ratio | Weight of Fraction |
|---|---|---|---|---|---|
| 1 | 50/56 | 104/106 | .9 mm | 4:1 | 15.7 |
| 2 | 65 | 124 | | 4:1 | 32.6 |
| 3 | 65 | 126 | | 4:1 | 18.8 |
| 4 | 95 | 128 | | | 18.1 |
| 5 | 92 | 128 | .8 mm | | 3.8 |
| 6 | 95 | 133 | .75 | 9:1 | 12.9 |
| 7 | 95 | 137 | .6 | 9:1 | 16.0 |
| 8 | 95 | 133 | .6 | 1:1 | 31.4 |
| 9 | 95 | 133 | .6 | 1:1 | 27.8 |
| 10 | 92 | 136 | .5 | 1:1 | 22.9 |
| 11 | 92 | 136 | .5 | 1:1 | 29.1 |
| 12 | 96 | 137 | .5 | 1:1 | 30.4 |
| 13 | 94 | 143 | .5 | 1:1 | 29.9 |
| 14 | 94 | 146 | .5 | 1:1 | 28.5 |
| 15 | 94 | 151 | .5 | 1:1 | 30.8 |
| 16 | 98 | 165 | .5 | 1:1 | 30.0 |
| 17 | 95 | 180 | .5 | 1:1 | 27.2 |

FIG. 10A is the GLC profile of the crude reaction product (conditions: ⅛"×10' 10% SE 30 packed column programmed at 120°-220° C. at 16° C. per minute).

FIG. 10B is the GLC profile for fraction 8 of the foregoing distillation (conditions: ⅛"×10' 10% SE 30 packed column programmed at 220° C. isothermal).

FIG. 11 is the NMR spectrum for fraction 10 of the foregoing distillation.

FIG. 12 is the infra-red spectrum for fraction 10 of the foregoing distillation.

The resulting product having the structure:

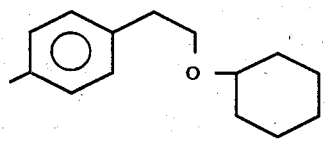

has an interesting intense, burnt fruit aroma.

EXAMPLE XVIII

Field tests are made each time using 100 male and 100 female Lasioderma serricorne (F.) cigarette beetles. The beetles were released at a certain distance from the source of attraction which was treated with one of the cyclohexyl phenethylether derivatives prepared according to either Example XVI or XVII. Further, felled trees having already been contaminated with the respective beetles are positioned at both sides of the starting point. After a certain period of time the amount of insects gathered at the source of attraction was determined thus indicating the effectiveness of the pheromonal mixture according to the invention.

Field tests with Lasioderma serricorne (F.) are made whereby the distance between the starting point and the source of attraction is 50 meters. Four independent field tests were made whereby 42% of the male beetles and 46% of the female beetles gathered at each catch tree. The concentration of insects at the catch tree was 55% of the male insects and 58% of the female insects. In all these tests the catch tree was impregnated with a 0.7% ethanolic solution of one of the cyclohexyl phenethylether derivatives of either Example XVI or XVII (7 grams of cyclohexyl phenethylether derivative per 92 grams of 95% aqueous ethanol).

EXAMPLE XIX

During two consecutive days several felled oak trees surrounding the field of tobacco plants were treated with 250 mg of one of the phenethyl cyclohexylether derivatives of either Example XVI or XVII in 1.0% ethanolic solution. These trees were exposed in an area which were contaminated with Lasioderma serricorne (F.). After 3 to 4 days 100 beetles per square meter were observed on the logs. Other untreated logs or trees in the direct neighborhood of the treated logs or trees showed very few (about 12) insects per square meter on the average while other trees at a distance of 10 to 20 meters showed no contamination.

EXAMPLE XX

In a large test field, mixtures of one of the cyclohexyl phenethylether derivatives of Example XVI or XVII in admixture with different DDT preparation, fluorine-containing mixtures and arsenic-containing mixtures as well as hexachlorocyclohexane were used. These mixtures contained also small amounts of surface active agents and carriers. The mixtures were applied to catch trees namely logs of oak trees in an area of tobacco plants contaminated with *Lasioderma serricorne (F.)*. The distance between the catch trees was always 200 meters. After 8 days there was no contamination either in the tobacco fields or around the oak trees. About 92% of the *Lasioderma serricorne (F.)* insects were destroyed. Surprisingly, it was found that after the fourth day the attracting effect was not diminished in spite of dead insects being present. Furthermore, in those areas where one of the cyclohexyl phenethylether derivatives of Example XVI or XVII was used alone, the average number of insects destroyed was about 80% which in itself is surprising. Thus, one of the cyclohexyl phenethylether derivatives of Example XVI or XVII not only acts as a pheromone but also as an insecticide. Furthermore, the entire area wherein one of the cyclohexyl phenethylether derivatives of Example XVI or XVII was used had a faint, pleasant aroma (floral in the case of the cyclohexyl phenethylether derivative of Example XVI and fruity in the case of the cyclohexyl phenethylether derivative of Example XVII) covering any adverse and esthetically displeasing aroma of any other insecticides that were used.

EXAMPLE XXI

The following mixture is prepared:

| Ingredient | Parts by Weight |
| --- | --- |
| Phenylacetic acid | 70.0 |
| Coumarin | 20.0 |
| Phenylethylphenyl acetate | 100.0 |
| Phenyl ethyl alcohol | 5.0 |
| Benzyl benzoate | 100.0 |
| Dimethylphenylethyl carbinol | 10.0 |
| Methyl anthranilate | 5.0 |
| Beta ionone | 10.0 |
| Cyclohexyl hydrotropyl ether produced according to Example XVI | 30.0 |

The cyclohexyl hydrotropyl ether prepared according to Example XVI imparts the floral, green, galbanum-like and fruity aroma to this honey fragrance while giving it a very warm undertone and imparting a very long lasting floral top note to this fragrance.

EXAMPLE XXII

PREPARATION OF A COSMETIC POWDER COMPOSITION

A cosmetic powder is prepared by mixing in a ball mill 100 grams of talcum powder with 0.25 grams of the perfume composition prepared according to Example XXI. It has an excellent floral aroma.

EXAMPLE XXIII

PERFUMED LIQUID DETERGENT

Concentrated liquid detergents (Lysine salt of n-dodecylbenzene sulfonic acid as more specifically described in U.S. Pat. No. 3,948,818 issued on Apr. 6, 1976) with floral aroma nuances and green, galbanum-like and fruity topnotes are prepared containing 0.10%, 0.15% and 0.20% of the fragrance prepared according to Example XXI. They are prepared by adding and homogeneously mixing the appropriate quantity of fragrance formulation prepared according to Example XXI in the liquid detergent. The detergents all possess excellent floral aromas with green, galbanum-like and fruity nuances, the intensity increasing with greater concentrations of perfume composition prepared according to Example XXI.

EXAMPLE XXIV

PREPARATION OF A COLOGNE AND HANDKERCHIEF PERFUME

The composition prepared according to Example XXI is incorporated into a cologne at concentrations of 2.0%, 2.5%, 3.0%, 4.0%, 4.5% and 5.0% in 80%, 85%, 90% and 95% aqueous food grade ethanol and into handkerchief perfumes at concentrations of 15%, 20% and 30% (in 80%, 85% and 95% aqueous food grade ethanol). A distinctive and definitive green, galbanum-like, fruity and full-bodied floral aroma is imparted to each of the colognes and to each of the handkerchief perfumes at all levels indicated.

EXAMPLE XXV

PREPARATION OF SOAP COMPOSITION 100 grams of soap chips are mixed with 1 gram of the formulation of Example XXI until a homogeneous composition is obtained. The homogeneous composition is heated under three atmospheres pressure at 180° C. for a period of three hours and the resulting liquid is placed into soap molds. The resulting soap cakes, on cooling, manifest excellent floral aromas with green, galbanum-like and fruity nuances that are very long lasting.

EXAMPLE XXVI

PREPARATION OF A SOLID DETERGENT COMPOSITION

A detergent is prepared from the following ingredients according to Example I of Canadian Pat. No. 1,007,948:

| | Percent by Weight |
| --- | --- |
| "Neodol 45-11" (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate free" detergent. A total of 100 grams of this detergent is admixed with 0.15 grams of the honey based perfume of Example XXI. Each of the detergent samples have an excellent floral honey-like, green, galbanum-like and fruity aroma.

EXAMPLE XXVII

DRYER-ADDED FABRIC SOFTENER ARTICLE

Utilizing the procedure of Example I at column 15 of U.S. Pat. No. 3,632,396, a nonwoven cloth substrate useful as a dryer-added fabric softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   - 57% $C_{20-22}$ HAPS
   - 22% isopropyl alcohol
   - 20% antistatic agent
   - 1% of cyclohexyl hydrotropyl ether prepared according to Example XVI A fabric softening composition prepared as set forth above having a green, galbanum-like and fruity and generally floral aroma characteristic consists of a substrate having a weight of about 3 grams per 100 square inches, a substrate coating of about 1.85grams per 100 square inches of substrate and an outer coating of about 1.4 grams per 100 square inches of substrate, thereby providing a total aromatized substrate and outer coating weight ratio of about 1:1 by weight of the substrate. A pleasant floral aroma is imparted in a pleasant manner to the head space in the dryer on operation thereof using the said dryer-added fabric softening nonwoven fabric.

EXAMPLE XXVIII

A liquid detergent composition prepared according to Example IV of United Kingdom Pat. No. 1,498,520 whereby the following ingredients are admixed:

| Ingredient | Weight % |
| --- | --- |
| Coconut alcohol ethoxylate | 30% |
| Linear alkyl benzene sulfonate, triethanolamine salt (alkyl = $C_{11.8}$ avg.) | 8% |
| Potassium chloride | 3% |
| Triethanolamine | 3% |
| Triethanolammonium citrate | 2% |
| Ethyl alcohol | 5% |
| Soil release ether "D" | 1.0% |
| Cyclohexyl hydrotropyl ether prepared according to Example XVI | 5.0% |
| Water | Balance |

The soil release ether "D" is defined according to Table II on page 15 of United Kingdom Pat. No. 1,498,520.

This composition is prepared by admixing all of the ingredients exclusive of soil release ether "D" and agitating the mixture until all electrolytes are dissolved. Soil release ether "D" is then admixed with the solution in the form of a dry powder which passes through a 150 mesh standard sieve. The resulting composition is in the liquid state and is easily pourable. The composition is found not to redden on contact with plastic bottles, does not gel when diluted with water and has a long-lasting aroma which can be described as green, galbanum-like, fruity and rich floral and rather long lasting. Indeed, the aroma lasts for several weeks when exposed to the atmosphere.

This composition is added to an aqueous laundrying bath at a concentration of 0.20% (weight) at a temperature of 55° C., water hardness 7 grains per gallon and a pH of 10.0. Polyester and mixed polyester/cotton fabrics are laundered in the bath for a period of 10 minutes after which the fabrics are thoroughly rinsed with fresh water and dried at ambient temperatures. The fabrics are provided with a soil release finish. The head space above the fabrics has a pleasant faint aroma which can be described as floral, green, galbanum-like and fruity and also rather long lasting (about 3 days).

EXAMPLE XXIX

PREPARATION OF A COSMETIC POWDER COMPOSITION

A cosmetic powder is prepared by admixing in a ball mill, 100 grams of talcum powder with 0.25 grams of cyclohexyl hydrotropyl ether prepared according to Example XVI. The resulting cosmetic powder has an excellent green, floral, galbanum-like and fruity aroma which is very long lasting.

EXAMPLE XXX

PERFUMED LIQUID DETERGENT

Concentrated liquid detergents (Lysine salt of n-dodecylbenzene sulfonic acid as more specifically described in U.S. Pat. No. 3,948,818 issued on Apr. 6, 1976) with floral, green, galbanum-like and fruity aroma are prepared containing 0.10%, 0.15%, 0.20% and 0.25% of cyclohexyl hydrotropyl ether prepared according to Example XVI. They are prepared by adding and homogeneously admixing the appropriate quantity of cyclohexyl hydrotropyl ether in the liquid detergent. The detergents all possess intense, long-lasting floral, green, galbanum-like and fruity aroma characteristics.

EXAMPLE XXXI

PREPARATION OF COLOGNES AND HANDKERCHIEF PERFUMES

Cyclohexyl hydrotropyl ether prepared according to Example XVI is incorporated into colognes at concentrations of 2.0%, 2.5%, 3.0%, 3.5%, 4.0% and 4.5% in 80%, 85%, 90% and 95% aqueous food grade ethanol; and into handkerchief perfumes at concentrations of 15%, 20%, 25% and 30% (in 80%, 90% and 95% aqueous ethanol). Distinctive floral, green, galbanum-like and fruity aroma nuances which are very long lasting on dry-out (46 hours) are imparted to the colognes and to the handkerchief perfumes at the various levels indicated above.

What is claimed is:

1. A method of attracting and destroying *Lasioderma serricorne* (F.) comprising applying to an area contaminated with said *Lasioderma serricorne* (F.) at least one compound defined according to the structure:

wherein $R_1$, $R_2$, $R_3$ and $R_4$ are the same or different and each represents methyl or hydrogen with the proviso that one of $R_1$, $R_2$, $R_3$ and $R_4$ is methyl and the other three of $R_1$, $R_2$, $R_3$ and $R_4$ are hydrogen, said attractant being applied to said area in an amount sufficient to attract said *Lasioderma serricorne* (F.).

2. The method of claim 1 wherein the amount of said attractant applied to said area is in an amount (a) sufficient to attract said *Lasioderma serricorne* (F.) and (b) sufficient to substantially destroy said *Lasioderma serricorne* (F.) thus attracted.

3. The method of claim 1 wherein the attractant applied to the area is in an amount (a) sufficient to attract said *Lasioderma serricorne* (F.), (b) sufficient to destroy said *Lasioderma serricorne* (F.) substantially, and (c) sufficient to negate any adverse aromas of any other materials in said area and augment or enhance or impart a floral aroma to said area.

* * * * *